United States Patent
Khan et al.

(10) Patent No.: US 7,175,657 B2
(45) Date of Patent: Feb. 13, 2007

(54) AAA DEVICE HAVING CONNECTED BIFURCATED LEGS

(75) Inventors: Isaac J. Khan, Bridgewater, NJ (US); Jin S. Park, Parsippany, NJ (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

(21) Appl. No.: 11/191,104

(22) Filed: Jul. 27, 2005

(65) Prior Publication Data

US 2006/0025851 A1 Feb. 2, 2006

Related U.S. Application Data

(60) Provisional application No. 60/591,650, filed on Jul. 28, 2004.

(51) Int. Cl.
*A61F 2/06* (2006.01)
(52) U.S. Cl. .................. 623/1.35; 623/1.12; 623/1.13; 623/1.15
(58) Field of Classification Search ................ 623/1.35
See application file for complete search history.

(56) References Cited

U.S. PATENT DOCUMENTS

| 5,197,976 | A | 3/1993 | Herweck et al. |
| 5,824,040 | A | 10/1998 | Cox et al. |
| 2003/0120338 | A1* | 6/2003 | Chobotov et al. ......... 623/1.36 |
| 2003/0195614 | A1 | 10/2003 | Ryan et al. |
| 2005/0113906 | A9* | 5/2005 | Bolduc et al. ............. 623/1.35 |

FOREIGN PATENT DOCUMENTS

EP 0722701 A1 7/1996

OTHER PUBLICATIONS

PCT Partial International Search Report PCT/US2005/026615 dated Nov. 9, 2005.
European Search Report EP 05254519 dated Oct. 27, 2005.

* cited by examiner

*Primary Examiner*—Tom Barrett
*Assistant Examiner*—David A. Izquierdo
(74) *Attorney, Agent, or Firm*—Carl J. Evens

(57) ABSTRACT

An abdominal aortic aneurysm device having an anchoring portion with attached bifurcated legs for increasing the column strength thereof. The bifurcated legs comprise staggered stents so that nesting is possible during delivery.

12 Claims, 4 Drawing Sheets

AAA DEVICE HAVING CONNECTED BIFURCATED LEGS

CROSS REFERENCE TO RELATED APPLICATIONS

This application claims the benefit of U.S. Provisional Patent Application Ser. No. 60/591,650 filed Jul. 28, 2004.

BACKGROUND OF THE INVENTION

1. Field of the Invention

The present invention relates to abdominal aortic aneurysm devices, and more particularly, to an abdominal aortic aneurysm device wherein the anchoring portion comprises bifurcated legs that are connected to one another.

2. Discussion of the Related Art

An aneurysm is an abnormal dilation of a layer or layers of an arterial wall, usually caused by a systemic collagen synthetic or structural defect. An abdominal aortic aneurysm is an aneurysm in the abdominal portion of the aorta, usually located in or near one or both of the two iliac arteries or near the renal arteries. The aneurysm often arises in the infrarenal portion of the diseased aorta, for example, below the kidneys. A thoracic aortic aneurysm is an aneurysm in the thoracic portion of the aorta. When left untreated, the aneurysm may rupture, usually causing rapid fatal hemorrhaging.

Aneurysms may be classified or typed by their position as well as by the number of aneurysms in a cluster. Typically, abdominal aortic aneurysms may be classified into five types. A Type I aneurysm is a single dilation located between the renal arteries and the iliac arteries. Typically, in a Type I aneurysm, the aorta is healthy between the renal arteries and the aneurysm and between the aneurysm and the iliac arteries.

A Type II A aneurysm is a single dilation located between the renal arteries and the iliac arteries. In a Type II A aneurysm, the aorta is healthy between the renal arteries and the aneurysm, but not healthy between the aneurysm and the iliac arteries. In other words, the dilation extends to the aortic bifurcation. A Type II B aneurysm comprises three dilations. One dilation is located between the renal arteries and the iliac arteries. Like a Type II A aneurysm, the aorta is healthy between the aneurysm and the renal arteries, but not healthy between the aneurysm and the iliac arteries. The other two dilations are located in the iliac arteries between the aortic bifurcation and the bifurcations between the external iliacs and the internal iliacs. The iliac arteries are healthy between the iliac bifurcation and the aneurysms. A Type II C aneurysm also comprises three dilations. However, in a Type II C aneurysm, the dilations in the iliac arteries extend to the iliac bifurcation.

A Type III aneurysm is a single dilation located between the renal arteries and the iliac arteries. In a Type III aneurysm, the aorta is not healthy between the renal arteries and the aneurysm. In other words, the dilation extends to the renal arteries.

A ruptured abdominal aortic aneurysm is presently the thirteenth leading cause of death in the United States. The routine management of abdominal aortic aneurysms has been surgical bypass, with the placement of a graft in the involved or dilated segment. Although resection with a synthetic graft via transperitoneal or retroperitoneal procedure has been the standard treatment, it is associated with significant risk. For example, complications include perioperative myocardial ischemia, renal failure, erectile impotence, intestinal ischemia, infection, lower limb ischemia, spinal cord injury with paralysis, aorta-enteric fistula, and death. Surgical treatment of abdominal aortic aneurysms is associated with an overall mortality rate of five percent in asymptomatic patients, sixteen to nineteen percent in symptomatic patients, and is as high as fifty percent in patients with ruptured abdominal aortic aneurysms.

Disadvantages associated with conventional surgery, in addition to the high mortality rate, include an extended recovery period associated with the large surgical incision and the opening of the abdominal cavity, difficulties in suturing the graft to the aorta, the loss of the existing thrombosis to support and reinforce the graft, the unsuitability of the surgery for many patients having abdominal aortic aneurysms, and the problems associated with performing the surgery on an emergency basis after the aneurysm has ruptured. Further, the typical recovery period is from one to two weeks in the hospital and a convalescence period, at home, ranging from two to three months or more, if complications ensue. Since many patients having abdominal aortic aneurysms have other chronic illnesses, such as heart, lung, liver and/or kidney disease, coupled with the fact that many of these patients are older, they are less than ideal candidates for surgery.

The occurrence of aneurysms is not confined to the abdominal region. While abdominal aortic aneurysms are generally the most common, aneurysms in other regions of the aorta or one of its branches are possible. For example, aneurysms may occur in the thoracic aorta. As is the case with abdominal aortic aneurysms, the widely accepted approach to treating an aneurysm in the thoracic aorta is surgical repair, involving replacing the aneurysmal segment with a prosthetic device. This surgery, as described above, is a major undertaking, with associated high risks and with significant mortality and morbidity.

Over the past five years, there has been a great deal of research directed at developing less invasive, endovascular, i.e., catheter directed, techniques for the treatment of aneurysms, specifically abdominal aortic aneurysms. This has been facilitated by the development of vascular stents, which can and have been used in conjunction with standard or thin-wall graft material in order to create a stent-graft or endograft. The potential advantages of less invasive treatments have included reduced surgical morbidity and mortality along with shorter hospital and intensive care unit stays.

Stent-grafts or endoprostheses are now Food and Drug Administration (FDA) approved and commercially available. Their delivery procedure typically involves advanced angiographic techniques performed through vascular accesses gained via surgical cut down of a remote artery, which may include the common femoral or brachial arteries. Over a guidewire, the appropriate size introducer will be placed. The catheter and guidewire are passed through the aneurysm. Through the introducer, the stent-graft will be advanced to the appropriate position. Typical deployment of the stent-graft device requires withdrawal of an outer sheath while maintaining the position of the stent-graft with an inner-stabilizing device. Most stent-grafts are self-expanding; however, an additional angioplasty procedure, e.g., balloon angioplasty, may be required to secure the position of the stent-graft. Following the placement of the stent-graft, standard angiographic views may be obtained.

Due to the large diameter of the above-described devices, typically greater than twenty French (3F=1 mm), arteriotomy closure typically requires open surgical repair. Some procedures may require additional surgical techniques, such as hypogastric artery embolization, vessel ligation, or surgical bypass in order to adequately treat the aneurysm or to maintain blood flow to both lower extremities. Likewise, some procedures will require additional advanced catheter directed techniques, such as angioplasty, stent placement and embolization, in order to successfully exclude the aneurysm and efficiently manage leaks.

While the above-described endoprostheses represent a significant improvement over conventional surgical techniques, there is a need to improve the endoprostheses, their method of use and their applicability to varied biological conditions. Accordingly, in order to provide a safe and effective alternate means for treating aneurysms, including abdominal aortic aneurysms and thoracic aortic aneurysms, a number of difficulties associated with currently known endoprostheses and their delivery systems must be overcome. One concern with the use of endoprostheses is the prevention of endo-leaks and the disruption of the normal fluid dynamics of the vasculature. Devices using any technology should preferably be simple to position and reposition as necessary, should preferably provide an acute, fluid tight seal, and should preferably be anchored to prevent migration without interfering with normal blood flow in both the aneurysmal vessel as well as branching vessels. In addition, devices using the technology should preferably be able to be anchored, sealed, and maintained in bifurcated vessels, tortuous vessels, highly angulated vessels, partially diseased vessels, calcified vessels, odd shaped vessels, short vessels, and long vessels. In order to accomplish this, the endoprostheses should preferably be highly durable, extendable and re-configurable while maintaining acute and long-term fluid tight seals and anchoring positions.

The market today is populated by devices approximately 20F and greater requiring the need for a surgical cut-down approach utilizing catheters, guidewires and accessory devices which substantially eliminate the need for open surgical intervention. Although the cut-down approach significantly reduces the acute complications that often accompany open surgical intervention, the ultimate goal and the market trend is to reduce delivery system profiles and to be able to perform the procedure of delivering an endoprosthesis percutaneously, as by the Seldinger technique, which eliminates the need for the cut-down procedure.

In order to reduce profile, the stents comprising the bifurcated legs are staggered relative to one another so that they are nested during delivery. By staggering the stent components of the bifurcated section, the column strength of each leg may be somewhat compromised, however, due to the spacing between the stent components which in turn may lead to a cannulation problem during deployment. This problem may be overcome by connecting the two legs together to improve column strength during deployment.

SUMMARY OF THE INVENTION

The present invention overcomes the disadvantages associated with larger endoprostheses as briefly described above.

In accordance with one aspect, the present invention is directed to an endoprosthesis. The endoprosthesis comprises a cranial section having a substantially tubular structure configured to anchor and seal the endoprosthesis within a vessel, a caudal section having at least two legs in fluid communication with the cranial section, the at least two legs each comprising a substantially tubular structure, graft material attached to at least a portion of the cranial section and to the at least two legs thereby forming at least two fluid flow conduits and a connection means for joining the at least two fluid flow conduits.

In accordance with another aspect, the present invention is directed to an endoprosthesis. The endoprosthesis comprises a cranial section having a substantially tubular structure configured to anchor and seal the endoprosthesis within a vessel, a caudal section having at least two legs in fluid communication with the cranial section, the at least two legs each comprising a substantially tubular structure and a graft material attached to at least a portion of the cranial section and to the at least two legs thereby forming at least two fluid flow conduits, the at least two fluid flow conduits being configured to nest together during delivery.

The endoprosthesis of the present invention offers a number of advantages over existing devices. The endoprosthesis may be anchored and sealed supra or infra-renally. The stents comprising the bifurcated legs are staggered relative to one another so that they are nested during delivery, thereby reducing the overall profile of the device. In addition, the endoprosthesis of the present invention has better overall wear resistance due to the elimination of stents. The bifurcated legs are connected together to improve their column strength. Increasing the column strength is important when connecting the endolegs for bypassing the aneurysm. In addition, the connected legs make it easier to attach the endolegs. The connection between the bifurcated legs may be temporary or permanent. The temporary connection may be made by biodegradeable sutures.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

The present invention is directed to an endovascular graft which may be utilized as a component in a system for use in treating or repairing aneurysms. Systems for treating or repairing aneurysms such as abdominal aortic aneurysms and thoracic aortic aneurysms come in many forms. A typical system includes an anchoring and/or sealing component which is positioned in healthy tissue above the aneurysm and one or more grafts which are in fluid communication with the anchoring and/or sealing component and extend through the aneurysm and anchor in healthy tissue below the aneurysm. Essentially, the grafts are the components of the system that are utilized to establish a fluid flow path from one section of an artery to another section of the same or different artery, thereby bypassing the diseased portion of the artery. Current systems are preferably percutaneously delivered and deployed.

The present invention is directed to the anchor and sealing component of the endovascular graft or endoprosthesis. Essentially, the endovascular graft of the present invention comprises a number of components that make up a modular system. Although the overall endovascular graft comprises a number of components, the challenges associated with these types of systems include profile, flexibility and accessibility. Loading an abdominal aortic aneurysm repair system or endovascular graft in a 13F delivery apparatus is not a simple task considering the amount of material that has to be delivered with such components. This is especially true of the anchoring and sealing component. The anchoring and sealing component comprises a trunk section and a bifurcated section wherein the two legs are supported by metallic stents. There are a number of design features that may be built into the anchoring and sealing component of the endovascular graft that may be utilized to reduce its profile, thereby making it a truly percutaneous device ((13F); namely, leaving spaces between the stent components in each of the legs and staggering the position of the stent components in each of the legs such that no two stent components line up. In this manner, the two legs of the bifurcated section may be nested during deployment thereby reducing the overall profile of the system. It is important to note, however, that by staggering the stent components of the bifurcated section, the column strength of each leg may be somewhat compromised due to the spacing between the stent components which in turn may lead to a cannulation problem during deployment. This problem may be overcome by connecting the two legs together to improve column strength during deployment.

Figure 1:
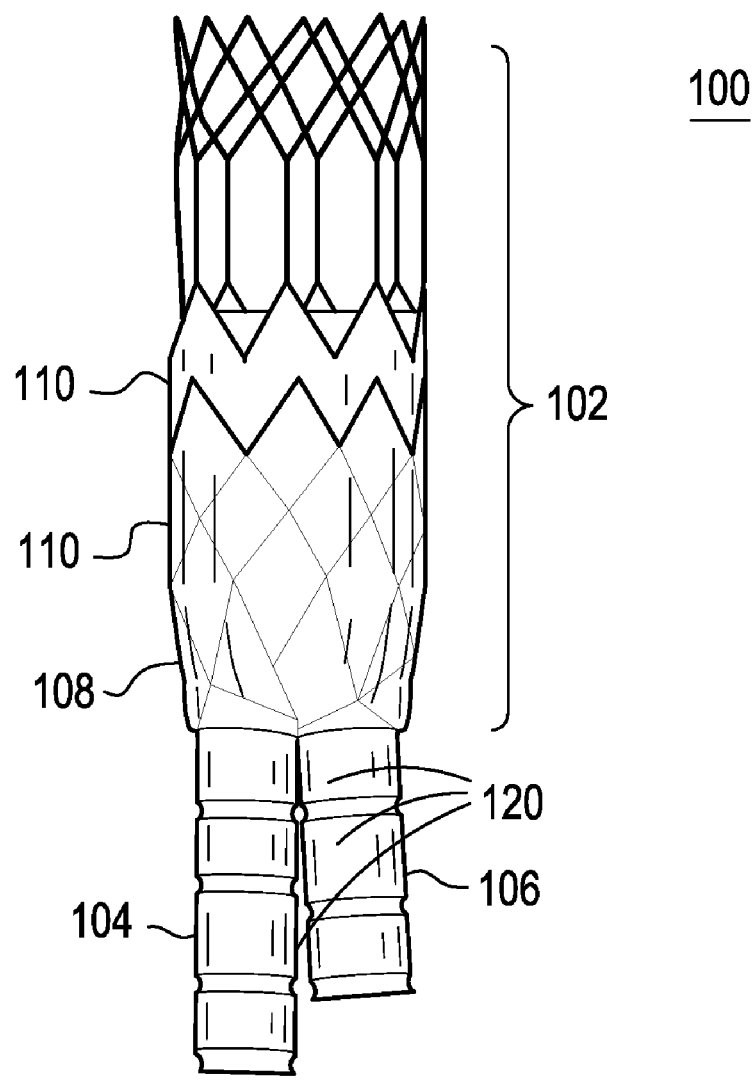
FIG. 1 is a diagrammatic representation of the exemplary anchoring and sealing prosthesis in accordance with the present invention.

Referring now to FIG. 1, there is illustrated an exemplary embodiment of an anchoring and sealing component 100 in accordance with the present invention. As illustrated, the anchoring and sealing component 100 comprises a trunk section 102 and a bifurcated section, including two legs 104, 106. Graft material 108 is affixed to at least a portion of the trunk section 102 and all of the legs 104, 106. The graft material is attached to various portions of the underlying structure by sutures 110. As illustrated, the graft material 108 is affixed with a continuous stitch pattern on the end of the trunk section 102 and by single stitches elsewhere. It is important to note that any pattern may be utilized and other devices, such as staples, may be utilized to connect the graft material 108 to the underlying structure. The sutures 110 may comprise any suitable biocompatible material that is preferably highly durable and wear resistant.

Figure 2:
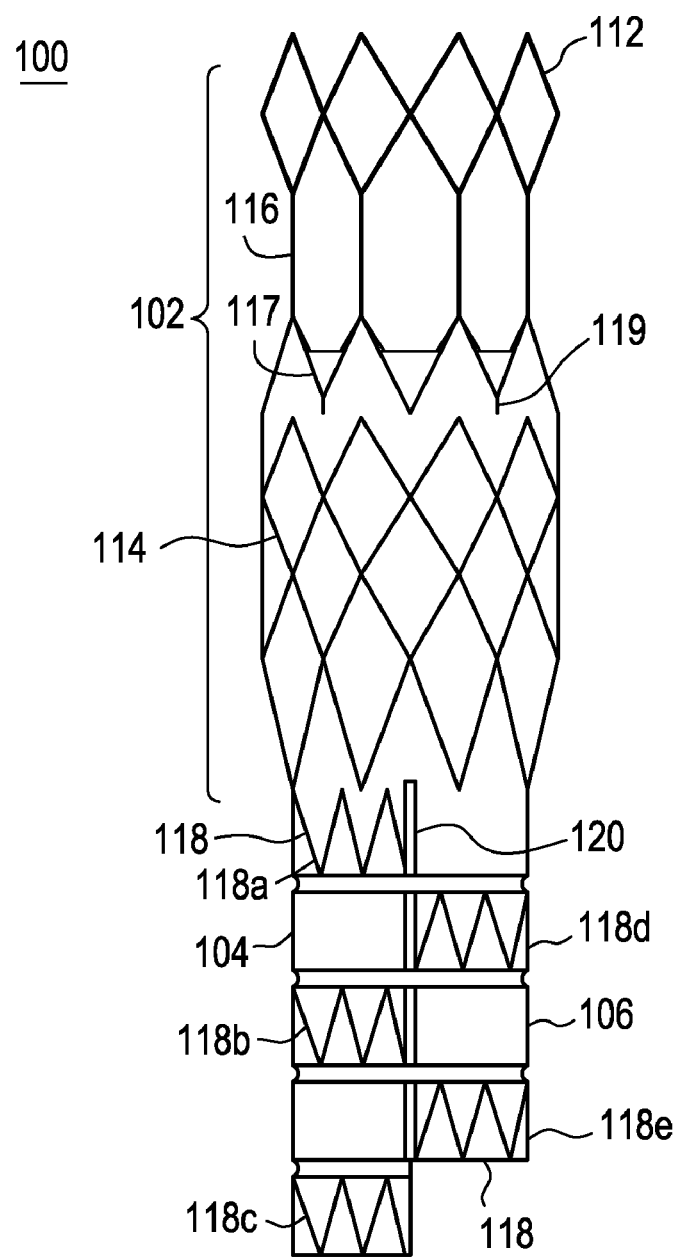
FIG. 2 is a diagrammatic representation of the exemplary anchoring and sealing prosthesis with no graft material in accordance with the present invention.

The underlying structure of the trunk section 102, as illustrated in FIG. 2, comprises a substantially tubular stent structure or lattice comprising multiple stent sections. The stent or lattice structure comprises a single row of diamond elements 112 on one end, multiple rows of diamond elements 114 on the other end, a plurality of longitudinal struts 116 and a single, substantially zigzag shaped stent element 117. The plurality of longitudinal struts 116 are connected to the apexes of the diamond elements 112. The single, substantially zigzag shaped stent element 117 comprises a number of barbs 119 protruding therefrom for anchoring. This exemplary embodiment may be utilized for anchoring and sealing in positions wherein there are branches off the main artery. For example, this exemplary embodiment may be utilized for supra-renal anchoring. Accordingly, the graft material 108 is only attached below the longitudinal struts 116 so that blood may flow into the renal arteries from the aorta. Infra-renal designs are also possible.

The underlying structure of the bifurcated section, as illustrated in FIG. 2, comprises a plurality of individual, substantially tubular stent elements 118. Each stent element 118 comprises a substantially zigzag pattern. As illustrated, leg 104 comprises three stent elements 118a, 118b, 118c and leg 106 comprises two stent elements 118d, 118e. Also illustrated is the fact that the stent elements do not line up and the legs are of two different lengths. As stated above, this design allows for nesting of the legs 104, 106 such that the profile of the device is reduced.

In order to compensate for the missing stent elements, the legs are connected at the bifurcation as illustrated in FIG. 1. The legs 104, 106 may be connected in any suitable manner. In the exemplary embodiment, the two legs 104, 106 are connected by suturing them together. The sutures 120 connect the graft material 108 on each leg 104, 106 together. The sutures may be non-biodegradable or biodegradable. Biodegradable sutures would dissolve over time thereby allowing the two legs to move independently.

Figure 3:
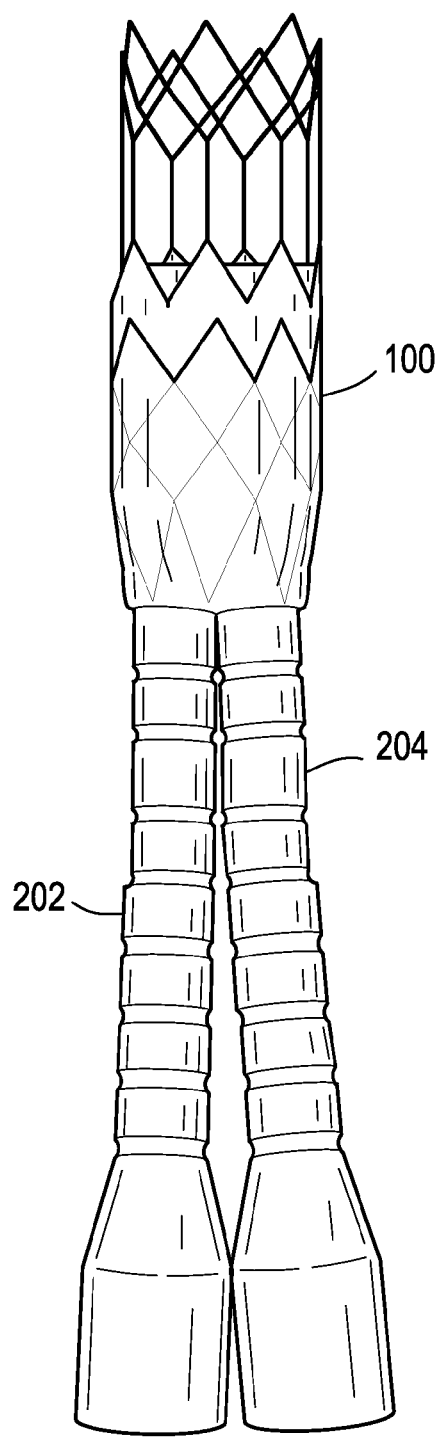
FIG. 3 is a diagrammatic representation of an exemplary abdominal aortic aneurysm repair device in accordance with the present invention.
Figure 4:
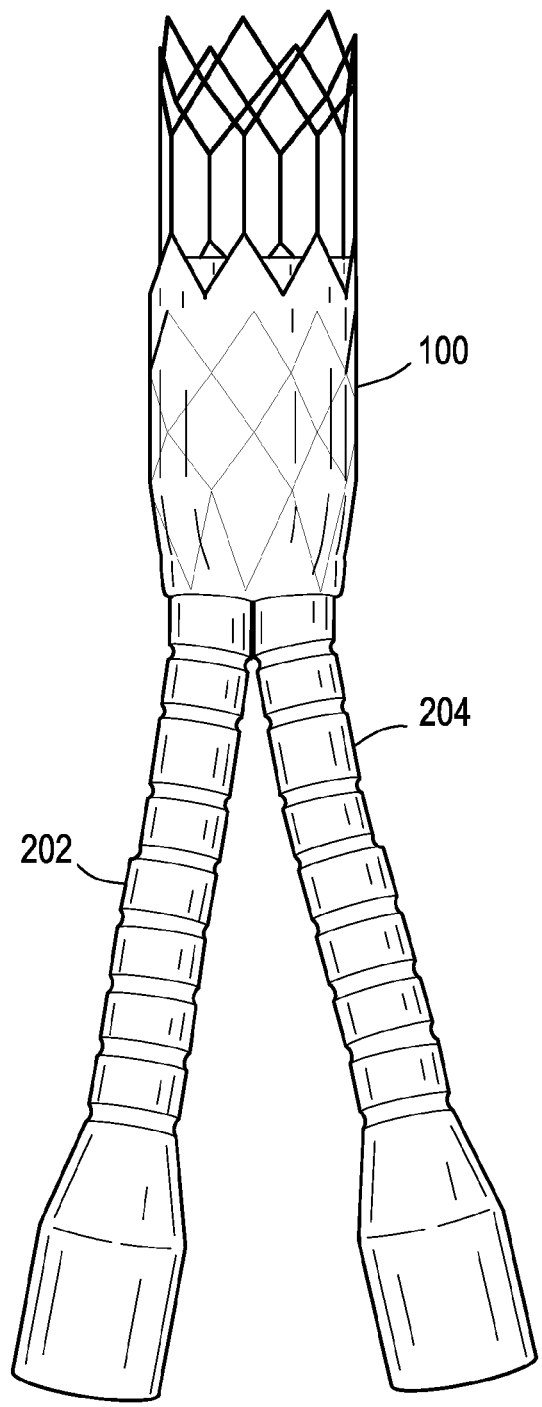
FIG. 4 is a diagrammatic representation of an exemplary abdominal aortic aneurysm repair device with the legs separated in accordance with the present invention.

FIGS. 3 and 4 illustrate the entire endovascular graft for repairing an abdominal aortic aneurysm. As may be seen, the entire endovascular graft comprises the anchoring and sealing component 100 and two grafts or endolegs 202 and 204. The grafts 202 and 204 each comprise a plurality of stent elements and graft material. The ends of the endolegs 202 and 204 may be flared for better anchoring and sealing in the down stream arteries. The flared section may be formed by flaring the last individual stent element. The endolegs 202, 204 are the bypass conduits through which the blood flows in the aneurysmal section of the artery. By eliminating the blood flow to the diseased section, the pressure is reduced and thus there is less of a chance of the aneurysm rupturing.

The stent segments of the present invention may be formed from any number of suitable biocompatible materials, including metals, polymers and ceramics. In a preferred embodiment, the stents are preferably self-expandable and formed from a shape memory alloy. Such an alloy may be deformed from an original, heat-stable configuration to a second, heat-unstable configuration. The application of a desired temperature causes the alloy to revert to an original heat-stable configuration. A particularly preferred shape memory alloy for this application is binary nickel titanium alloy comprising about 55.8 percent Ni by weight, commercially available under the trade designation NITINOL. This NiTi alloy undergoes a phase transformation at physiological temperatures. A stent made of this material is deformable when chilled. Thus, at low temperatures, for example, below twenty degrees centigrade, the stent is compressed so that it can be delivered to the desired location. The stent may be kept at low temperatures by circulating chilled saline solutions. The stent expands when the chilled saline is removed and it is exposed to higher temperatures within the patient's body, generally around thirty-seven degrees centigrade.

In preferred embodiments, each stent is fabricated from a single piece of alloy tubing. The tubing is laser cut, shape-set by placing the tubing on a mandrel, and heat-set to its desired expanded shape and size.

In preferred embodiments, the shape setting is performed in stages at five hundred degrees centigrade. That is, the stents are placed on sequentially larger mandrels and briefly heated to five hundred degrees centigrade. To minimize grain growth, the total time of exposure to a temperature of five hundred degrees centigrade is limited to five minutes. The stents are given their final shape set for four minutes at five hundred fifty degrees centigrade, and then aged to a temperature of four hundred seventy degrees centigrade to import the proper martensite to austenite transformation temperature, then blasted, as described in detail subsequently, before electropolishing. This heat treatment process provides for a stent that has a martensite to austenite transformation which occurs over a relatively narrow temperature range; for example, around fifteen degrees centigrade.

To improve the mechanical integrity of the stent, the rough edges left by the laser cutting are removed by combination of mechanical grit blasting and electropolishing. The grit blasting is performed to remove the brittle recast layer left by the laser cutting process. This layer is not readily removable by the electropolishing process, and if left intact, could lead to a brittle fracture of the stent struts. A solution of seventy percent methanol and thirty percent nitric acid at a temperature of minus forty degrees centigrade or less has been shown to work effectively as an electropolishing solution. Electrical parameters of the electropolishing are selected to remove approximately 0.00127 cm of material from the surfaces of the struts. The clean, electropolished surface is the final desired surface for attachment to the graft materials. This surface has been found to import good corrosion resistance, fatigue resistance, and wear resistance.

The graft material or component may be made from any number of suitable biocompatible materials, including woven, knitted, sutured, extruded, or cast materials comprising polyester, polytetrafluoroethylene, silicones, urethanes, and ultralight weight polyethylene, such as that commercially available under the trade designation SPECTRA™. The materials may be porous or nonporous. Exemplary materials include a woven polyester fabric made from DACRON™ or other suitable PET-type polymers.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope for the appended claims.

What is claimed is:

1. An endoprosthesis comprising:
   a trunk section configured to anchor and seal the endoprosthesis within a vessel, the trunk section further comprising a substantially tubular stent structure having a first and a second end, said stent having a single row of diamond elements at the first end, multiple rows of diamond elements towards the second end, a substantially zigzag element between the single row of diamond elements at the first end and the uppermost row of the multiple rows of diamond elements, and a plurality of longitudinal struts connecting the single row of diamond elements to the uppermost row of the multiple row of diamond elements; and
   a bifurcated section of two legs connected to the trunk section, wherein the two legs are supported by metallic stent components, the stent components include a plurality of individual substantially tubular stent elements, each of the tubular stent elements comprises a substantially zigzag element, each of the two legs is comprised of a different number of the substantially tubular stent elements such that the stent elements in one of the two legs do not line up with the stent elements in the other of the two legs, the two legs being connected to one another via sutures and wherein graft material is attached to at least a portion of the trunk and all of the two legs, the sutures connect the graft material on each of the two legs together.

2. The endoprosthesis of claim 1, wherein the stent components of each of the two legs are staggered relative to each other such that no two stent components line up with another stent component.

3. The endoprosthesis of claim 1, further comprising spaces between the stent components in each of the two legs.

4. The endoprosthesis of claim 1, further comprising a connection connecting the two legs to improve columnar strength.

5. The endoprosthesis of claim 1, wherein the substantially zigzag element further comprises barbs protruding therefrom for anchoring the endoprosthesis.

6. The endoprosthesis of claim 1, wherein the graft material is attached below the longitudinal struts.

7. The endoprosthesis of claim 1, wherein the two legs are of different lengths.

8. The endoprosthesis of claim 1, wherein the sutures are biodegradable.

9. The endoprosthesis of claim 1, further comprising a flared end at an end of each of the two legs opposite the trunk.

10. The endoprosthesis of claim 9, wherein the flared end is comprised of flaring a last of the individual stent elements in each of the two legs.

11. The endoprosthesis of claim 1, wherein the stent components are comprised of any of metallic, polymeric and ceramic biocompatible materials.

12. The endoprosthesis of claim 1, wherein the stent components are comprised of shape memory material.

* * * * *